United States Patent [19]
Duncombe et al.

[11] Patent Number: 5,962,654
[45] Date of Patent: Oct. 5, 1999

[54] ALKOXYALKOXIDES AND USE TO FORM FILMS

[75] Inventors: Peter Richard Duncombe, Peekskill, N.Y.; Deborah Ann Neumayer, Danbury, Conn.

[73] Assignee: International Business Machines Operation, Armonk, N.Y.

[21] Appl. No.: 09/016,793

[22] Filed: Jan. 30, 1998

[51] Int. Cl.$^6$ .................................. C07F 5/00; C07F 7/00; C07F 2/00; C07F 19/00

[52] U.S. Cl. .................................. 534/15; 556/1; 556/42; 556/76; 556/81; 556/136; 556/146; 427/384

[58] Field of Search .................................. 556/42, 76, 81, 556/136, 146, 1; 534/15

[56] References Cited

U.S. PATENT DOCUMENTS

| | | | |
|---|---|---|---|
| 4,920,093 | 4/1990 | Nonaka et al. | 505/1 |
| 5,138,520 | 8/1992 | McMillan et al. | 361/311 |
| 5,328,718 | 7/1994 | Abe et al. | 427/126.3 |
| 5,423,285 | 6/1995 | Paz de Araujo et al. | 117/90 |
| 5,454,861 | 10/1995 | Hasegawa et al. | 106/2 |
| 5,456,945 | 10/1995 | McMillan et al. | 427/252 |
| 5,514,822 | 5/1996 | Scott et al. | 556/28 |
| 5,516,363 | 5/1996 | Azuma et al. | 106/287.18 |
| 5,540,772 | 7/1996 | McMillan et al. | 118/50 |
| 5,559,260 | 9/1996 | Scott et al. | 556/28 |

*Primary Examiner*—Porfirio Nazario-Gonzalez
*Attorney, Agent, or Firm*—Pollock, Vande Sande & Amernick; Daniel P. Morris

[57] ABSTRACT

Metal alkoxyalkoxides wherein the alkoxy portion has 3–6 carbon atoms and the alkoxide portion has 2–6 carbon atoms are provided and are useful in forming films on a substrate.

17 Claims, No Drawings

ALKOXYALKOXIDES AND USE TO FORM FILMS

TECHNICAL FIELD

The present invention is concerned with new metal alkoxyalkoxides and especially concerned with metal alkoxyalkoxides that can be used for fabricating thin films. Metal alkoxyalkoxide solutions of the present invention and especially mixtures of different metal alkoxyalkoxide solutions can be applied to a substrate and heated to form a thin film such as a metal oxide film. Metal oxide films formed according to the present invention find particular application as dielectric or ferroelectric layers in the microelectronics industry.

BACKGROUND OF INVENTION

Various metal oxide films have been suggested as dielectric or ferroelectric layers in the microelectronics industry. For instance, lead zirconate titanate, barium titanate, strontium bismuth tantalate, strontium bismuth niobate, and barium strontium titanate as well as other metal oxides have been suggested as the dielectric or ferroelectric capacitors used in memory cells. Metal oxide films such as $BaSrTiO_3$ (BST) films have many potential applications in dynamic random access memories (DRAM), nonvolatile random access memories (NVRAM), field effect transistor (FET) display technology and passive component packaging (interposer). Successful solution deposition of ferroelectrics or dielectrics such as $BaSrTiO_3$ (BST) depends on the availability of suitable precursors with appropriate reactivity, low cost and nontoxicity.

For example, Sol-gel deposition of BST and other dielectric metal oxide materials is typically conducted with short-chain alkoxides such as ethoxides, or isopropoxides. Short-chain alkoxides usually hydrolyze too readily to permit convenient handling and long term storage. These alkoxides will absorb ambient water from the atmosphere, which quickly hydrolyzes some of the material and can lead to precipitate formation.

Other liquid deposition routes to BST include metal-organic decomposition routes based on thermal decomposition of metal acetates. Acetate based chemistry typically requires higher annealing temperatures and passes through an oxocarbonate transition to form barium strontium titanate. In addition, acetate solutions are typically unstable and can gel within hours or days of mixing.

An improvement on short-chain alkoxides or MOD with acetates is sol-gel deposition with barium strontium and titanium methoxyethoxides. Barium titanium methoxyethoxides are known (J. -F. Campion, D. A. Payne, H. K. Chae, J. K. Maurin, S. R. Wilson, *Inorg. Chem.* Volume 30, pg. 3245, 1991; K. G. Caulton, M. H. Chisolm, S. R. Drake, J. C. Huffman, *J. Chem. Soc. Chem. Comm.*, pg. 1498 (1990) and have been fabricated into thin films (J. -F. Campion, D. A. Payne, H. K. Chae and Z. Xu, *Ceramic Trans.* Volume 22, pg. 477, 1991; M. H. Frey, D. A. Payne, *Appl. Phys. Lett.* Volume 63, pp. 2753, 1993). Strontium titanium 2-methoxyethoxides are known and have been fabricated into thin films (U. Selvarag, A. V. Prasadarao, S. Komarneni, R. Roy, *Materials Letters* Volume 23, pg. 123, 1995).

Methoxyethoxides hydrolyze more slowly than acetates or short chain alkolides, resulting in improved moisture tolerance and solvent stability. However, barium strontium titanium methoxyethoxide mixtures have limited solubility, limiting solution concentrations to less than 0.4 M. This limited solubility necessitates storage of dilute stock solutions, difficulty in spin coating or dipping thick layers, and solubility problems during extended storage, and precipitation during spin coating or dipping.

Barium titanium methoxyethoxides have been shown to form partially hydrolyzed clusters after exposure to trace amounts of water which leads to a degradation of the spin solution and results in films with poorer electrical properties. An additional problem associated with methoxyethanol is its tetragenic toxicity. Methoxyethanol is banned in many industrial applications and is listed as a hazardous waste product, limiting its usefulness for commercial applications.

SUMMARY OF INVENTION

An object of the present invention is to provide metal alkoxyalkoxides that exhibit increased solubility in organic solvents, reduced tendency to hydrolyze than prior art alkoxyalkoxides, along with enhanced safety upon use of the compounds. Compounds of the present invention also exhibit improved solution stability, longer shelf life and ability to spin thicker films per layer. A metal alkoxyalkoxide is a compound of the form $ML_a$, where M is a metal, L is an alkoxyalkoxide ligand, and a is a subscript indicating the number of units of the alkoxyalkoxide ligand required to correspond with the valence requirements of the metal. An alkoxyalcohol is distinguished from an alcohol by the existence of an ether linkage, C—O—C, in the hydrocarbon backbone of the alkoxyalcohol.

According to the present invention, the alkoxy portion of metal alkoxyalkoxide contains 3 to 7 carbon atoms. The alkoxide portion of the compounds of the present invention contains 2–6 carbon atoms. Suitable metals employed to form the novel alkoxyalkoxides of the present invention are metal selected from the group consisting of Group I, Group II, Group IIIB, Group IVA, Group V, Group VIIB and Group VIII metals.

The present invention is also concerned with solutions of the metal alkoxyalkoxides.

Another aspect of the present invention is solutions of mixtures of metal alkoxyalkoxides of the present invention with each other and/or with other metal alkoxyalkoxides.

A further aspect of the invention is forming films from solutions of the metal alkoxyalkoxides.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BEST AND VARIOUS MODES FOR CARRYING OUT INVENTION

The present invention is concerned with metal increased solubility in organic solvents, reduced tendency to hydrolyze than prior art alkoxyalkoxides along with enhanced safety upon use of the compounds.

According to the present invention, the alkoxy portion of metal alkoxyalkoxide contains 3 to 7 carbon atoms and includes propoxy, butoxy, pentoxy and heptoxy moieties with butoxy being preferred.

The alkoxide portion of the compounds of the present invention contains 2–6 carbon atoms, preferably 2–3 carbon atoms, and includes ethanol and propanol.

Examples of suitable alkoxyalkoxide portions of the compounds of the present invention are propoxyethanol, butoxyethanol, pentoxyethanol, heptoxyethanol, propoxypropanol, butoxypropanol, pentoxyproponal, and heptoxyproponal, and preferably butoxyethanol.

Suitable metals employed to form the novel alkoxyalkoxides of the present invention are metals selected from the group consisting of Group I, Group II, Group IIIB, Group IVA, Group V, Group VIIB and Group VIII metals.

Examples of suitable Group I metals include the Group IA alkali metals Li, Na and K; and the Group IB metals such as Cu.

Examples of suitable Group II metals include the Group IIA alkaline earth metals Mg, Ca, Sr and Ba; and Group IIB metals such as Zn.

Examples of suitable Group IIIB metals are Sc, Y and La.

An example of a suitable group IVA metal is Pb.

Examples of suitable Group V metals are Group VB metals such as Nb and Ta and Group VA metals such as Bi.

An example of a Group VIIE metal is Mn.

Examples of Group VIII metals are Fe, Ru, Co, Ni and Rh.

The preferred metals are the alkali metals, alkaline earth metals, Nb, Pb, Ta and Bi and most preferably Bi, Ba, Sr, Nb and Ta.

The metal alkoxyalkoxide can be synthesized by reacting the metal with an excess of the alkoxyalcohol, or by reacting a metal alkoxide with an excess of alkoxyalcohol or by reacting a metal halide salt with the lithium, sodium or potassium salt of the alkoxyalcohol. The reaction is typically carried out in a miscible solvent. Miscible solvents that may be used include hydrocarbons such as xylene, toluene, halgonated solvents such as chloroform, and alcohols such as methanol, ethanol, isopropanol, methoxyethanol, ethoxyethanol, propoxyethanol, butoxyethanol, pentoxyethanol, heptoxyethanol, methoxypropanol, ethoxypropanol, propoxypropanol, butoxypropanol, pentoxyproponal, and heptoxyproponal, preferably butoxyethanol.

For example, when an alkali earth (Group IA: Li, Na, K) metal or an alkaline earth (Group IIA: Mg, Ca, Sr, Ba) metal is added to an excess of alkoxyalcohol and heated, the following reaction occurs:

$$M + L \rightarrow ML_a + \tfrac{1}{2}H_2. \quad (1)$$

When a metal alkoxide is added to an excess of alkoxyalcohol and heated the following reaction occurs where A is an alkoxide:

$$MA_a + L \rightarrow ML_a + aA. \quad (2)$$

When a sufficiently reactive metal halide salt is added to an alkali earth metal (Group IA: Li, Na, K) salt of the alkoxyalcohol and heated, the following reactions occurs, where X is a halide, and N is alkali earth metal (Group IA: Li, Na, K):

$$MX_a + aNL \rightarrow ML_a + aNX. \quad (3)$$

The metal alkoxyalkoxides of the present invention are especially suitable for forming films on a substrate. Once the metal alkoxyalkoxide is formed, it can be dissolved into a miscible solvent such as those disclosed above and applied to a substrate. The coated substrate is thermally treated to densify the film. The coated substrate may be annealed to crystallize the film.

The substrate is typically heated to temperatures of about 200° C. to about 500° C., and more typically about 300° C. to about 400° C., for about 1 to about 15 minutes to thereby densify the film. The annealing is typically carried out at temperatures of about 500° C. to about 800° C., and more typically about 650° C. to about 750° C. for about 1 to about 60 minutes to thereby crystallize the film.

According to preferred aspects of the present invention, mixtures of the metal alkoxyalkoxides with each other or with other metal alkoxyalkoxides are employed to create mixed metal oxide layers. Other suitable metal alkoxyalkoxides that can be used in the mixtures with those of the present invention include alkoxyalkoxides of Ti, Zr, Al and Ga. Preferably, such alkoxyalkoxides contain 2–6 carbon atoms in the alkoxy moiety and 2–6 in the alkoxide moiety.

The alkoxides are typically present in the solution in amounts of about 0.01 molar to about 3 molar and preferably about 0.4 molar to about 2 molar.

The following non-limiting examples are presented to further illustrate the present invention.

EXAMPLE 1

Preparation of Ba(butoxyethoxide)$_2$

Under nitrogen, 25.2 g barium metal was added to 111 grams of butoxyethanol. The slurry was refluxed for 1 h to complete the reaction. The solution was cooled to room temperature, and filtered through a celite bed in vacuo. The filtrate was the barium butoxyethoxide stock solution with a concentration of 1.42 moles/liter or 22.69 weight percent of barium.

EXAMPLE 2

Preparation of Sr(butoxyethoxide)$_2$

Under nitrogen 26.1 g strontium metal was added to 293 g of butoxyethanol. The slurry was refluxed for 1 h to complete the reaction. The solution was cooled to room temperature, and filtered through a celite bed in vacuo. The filtrate was the strontium butoxyethoxide stock solution with a concentration of 0.919 moles/liter or 8.92 weight percent of strontium.

EXAMPLE 3

Preparation of Ti(butoxyethoxide)$_4$

Under nitrogen, 110 g titanium (IV) isopropoxide was added to 100 ml of butoxyethanol. The isopropanol was distilled away and an additional 100 ml of butoxyethanol was added and refluxed for 1 h. The solution was cooled to room temperature, and filtered through a celite bed in vacuo. The filtrate was the titanium butoxyethoxide stock solution with a final concentration of 1.53 moles/liter or 7.91 weight percent of titanium.

EXAMPLE 4

Fabrication of a $Ba_{0.7}Sr_{0.3}TiO_3$ Film with a Ba, Sr, Ti butoxyethoxide solution Under nitrogen, 11.11 g (0.0175 mol) barium butoxyethoxide stock solution (21.64 weight percent Ba), 8.57 g (0.0075 mol) strontium butoxyethoxide stock solution (7.67 weight percent Sr), 15.14 g (0.025 mol) and titanium butoxyethoxide stock solution (7.91 weight percent Ti) as prepared in Examples 1–3 were dissolved in butoxyethanol. The solution was stirred overnight at room temperature, filtered and diluted to 50 ml. The resultant 0.5M stock solution may be stored under nitrogen for several months without degradation. A spin solution affording 500 Å/layer films was prepared by diluting 3 parts $Ba_{0.7}Sr_{0.3}Ti$ stock solution with one part butoxyethanol. The spin solution was loaded into a syringe and a 0.45 μm and 0.2 μm Whatman syringe filters were attached. The solution was syringed onto $Pt/Ti/SiO_2/Si$ substrate until the substrate was completely wetted. The substrate was then spun for 60 sec at 2500 rpm. The coated substrate was dried on a hot plate at 325° C. for about 3 minutes and then annealed by rapid thermal processing at 700° C. for about 2 minutes. Additional layers were deposited as described above to fabricate thicker films. After annealing, Pt dots were evaporated onto the film and the capacitance across the film was measured. The resultant 3 and 4 layer samples with 1500 and 2100 Å thickness had dielectric constants of 200–340, dielectric losses of $10^{-1}$–$10^{-2}$, and leakage currents of $10^{-6}$–$10^{-8}$ $A/cm^2$ at 200 kHz.

EXAMPLE 5

Preparation of Ta(butoxyethoxide)$_5$

Under nitrogen with stirring, 53.13 g tantalum (V) ethoxide was added to 150 ml of butoxyethanol. The ethanol was distilled away and an additional 50 ml of butoxyethanol was added and refluxed for 1 h. The solution was cooled to room temperature, and filtered through a celite bed in vacuo. The filtrate was the tantalum butoxyethoxide stock solution.

EXAMPLE 6

Preparation of Bi(butoxyethoxide)$_3$

Under inert atmosphere, 28.9 g (0.244 mol) of butoxyethanol was added drop wise to a stirring suspension of 9.45 g (0.394 mol) sodium hydride in 100 mL of tetrahydrofuran. After stirring for 30 minute, the slurry was filtered through a celite bed. To the filtrate was added 25.0 g (0.0793 mol) of $BiCl_3$ dissolved in 100 ml of tetrahydrofuran. After stirring for 12 h, the tetrahydrofuran was removed in vacuo resulting in cloudy yellow slurry which was extracted with 250 ml of anhydrous toluene. The extract was filtered through a celite bed. The toluene was removed from the filtrate in vacuo resulting in a pale yellow oil which was extracted with 500 ml of pentane. The pentane extract was filtered through a celite bed and the pentane removed from the filtrate in vacuo resulting in a pale yellow liquid.

EXAMPLE 7

Preparation of Nb(butoxyethoxide)$_5$

Under nitrogen with stirring, 50.22 g niobium (V) ethoxide was added to 150 ml of butoxyethanol. The ethanol was distilled away and an additional 50 ml of butoxyethanol was added and refluxed for 1 h. The solution was cooled to room temperature, and filtered through a celite bed in vacuo. The filtrate was the niobium butoxyethoxide stock solution.

EXAMPLE 8

Fabrication of a $SrBi_2Ta_2O_2$ Film with a Sr, Bi, Ta butoxyethoxide solution

Under nitrogen, add 0.02 mol of a strontium butoxyethoxide stock solution, 0.04 mol bismuth butoxyethoxide stock solution, 0.04 mol of a titanium butoxyethoxide stock solution as prepared in Example 2, 6 and 5. Stir overnight at room temperature, filter and dilute to 100 ml. A spin solution was prepared by diluting 1 part $SrBi_2Ta_2$ stock solution with one part butoxyethanol. The spin solution was loaded into a syringe and a 0.45 μm and 0.2 μm Whatman syringe filters were attached. The solution was syringed onto $Pt/Ti/SiO_2/Si$ substrate until the substrate was completely wetted. The substrate was then spun for 60 sec at 2500 rpm. The coated substrate was dried on a hot plate at 300° C. and then annealed at 750° C. for about 30 min. Additional layers were deposited to fabricate thicker films.

EXAMPLE 9

Fabrication of a $Sr_{0.8}Bi_{2.2}Ta_2O_2$ Film with a Sr, Bi, Ta butoxyethoxide solution Under nitrogen, add 0.016 mol of a strontium butoyethoxide stock solution (Example 2), 0.044 mol bismuth butoxyethoxide stock solution (Example 6), 0.04 mol of a tantalum butoxyethoxide stock solution (Example 5). Stir overnight at room temperature, filter and dilute to 100 ml. A spin solution was prepared by diluting 1 part $Sr_{0.8}Bi_{2.2}Ta_2$ stock solution with one part butoxyethanol. The spin solution was loaded into a syringe and a 0.45 μm and 0.1 μm Whatman syringe filters were attached. The solution was syringed onto Pt/Ti/$SiO_2$/Si substrate until the substrate was completely wetted. The substrate was then spun for 60 sec at 2500 rpm. The coated substrate was dried on a hot plate at 300° C. and then annealed at 750° C. for 30 min. Additional layers were deposited to fabricate thicker films.

EXAMPLE 10

Fabrication of a $SrBi_2(Ta_{1.5}Nb_{0.5})O_2$ Film with a Sr, Bi, Ta, Nb butoxyethoxide solution Under nitrogen, add 0.02 mol of a strontium butoxyethoxide stock solution(Example 2), 0.04 mol bismuth butoxyethoxide stock solution (Example 6), 0.03 mol of a tantalum butoxyethoxide stock solution (Example 5) and 0.01 mol of a niobium butoxyethoxide solution. Stir overnight at room temperature, filter and dilute to 100 ml. A spin solution was prepared by diluting 1 part $Sr_{0.8}Bi_{2.2}Ta_2$ stock solution with one part butoxyethanol. The spin solution was loaded into a syringe and a 0.45 μm and 0.1 μm Whatman syringe filters were attached. The solution was syringed onto Pt/Ti/$SiO_2$/Si substrate until the substrate was completely wetted. The substrate was then spun for 60 sec at 2500 rpm. The coated substrate was dried on a hot plate at 300° C. and then annealed at 750° C. for 30 min. Additional layers were deposited to fabricate thicker films.

EXAMPLE 11

Fabrication of a $Bi_4Ti_3O_{12}$ Film with a Bi, Ti butoxyethoxide solution

Under nitrogen, 0.02 mol of a bismuth butoxyethoxide stock solution and 0.015 mol of a titanium butoxyethoxide stock solution as prepared in Examples 6 and 3 was mixed together and stirred overnight at room temperature. The solution was filtered and diluted to 100 mL with butoxyethanol. Stir overnight at room temperature, filter and dilute to 50 ml. A spin solution was prepared by diluting 1 part $Bi_4Ti_3$ stock solution with one part butoxyethanol. The spin solution was loaded into a syringe and a 0.45 μm and 0.2 μm Whatman syringe filters were attached. The solution was syringed onto Pt/Ti/$SiO_2$/Si substrate until the substrate was completely wetted. The substrate was then spun for 60 sec at 2500 rpm. The coated substrate was dried on a hot plate at 300° C. and then annealed by rapid thermal processing at 700° C. for 2 min. Additional layers were deposited to fabricate thicker films.

EXAMPLE 12

Preparation of Bi(butoxyethoxide)$_3$

Under nitrogen with stirring, 20 g bismuth (III) t-pentoxide was added to 50 ml of butoxyethanol. The t-pentanol was distilled away and an additional 50 ml of butoxyethanol was added and refluxed for 1 h. The solution was cooled to room temperature, and filtered through a celite bed in vacuo. The filtrate was the bismuth butoxyethoxide stock solution with a final concentration of 0.4 moles/liter of bismuth.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A metal alkoxyalkoxide wherein the alkoxy moiety of said alkoxyalkoxide has 3 to 7 carbon atoms, wherein the alkoxide moiety has 2 to 6 carbon atoms, and wherein the metal comprises at least one metal selected from the group consisting of Group I, Group II, Group IIIB, Group IVA, Group V, Group VIIB and Group VIII.

2. The metal alkoxyalkoxide of claim 1 wherein said alkoxy moiety is selected from the group consisting of propoxy, butoxy, pentoxy and heptoxy.

3. The metal alkoxyalkoxide of claim 1 wherein said alkoxy moiety is propoxy.

4. The metal alkoxyalkoxide of claim 1 wherein said alkoxide moiety is from ethanol and propanol.

5. The metal alkoxyalkoxide of claim 1 wherein the alkoxyalkoxide portion is an alcohol selected from the group consisting of propoxyethanol, butoxyethanol, pentoxyethanol, heptoxyethanol, propoxypropanol, butoxypropanol, pentoxypropanol and heptoxypropanol.

6. The metal alkoxyalkoxide of claim 1 being from butoxyethanol.

7. The metal alkoxyalkoxide of claim 1 wherein said metal is selected from the group consisting of alkali metal, alkaline earth metal, Nb, Pb, Ta and Bi.

8. The metal alkoxyalkoxide of claim 1 wherein said metal is selected from Bi, Ba and Sr.

9. The metal alkoxyalkoxide of claim 1 being Ba(butoxyethoxide)$_2$.

10. The metal alkoxyalkoxide of claim 1 being Sr(butoxyethoxide)$_2$.

11. The metal alkoxyalkoxide of claim 1 being Ta(butoxyethoxide)$_5$.

12. The metal alkoxyalkoxide of claim 1 being Bi(butoxyethoxide)$_3$.

13. The metal alkoxyalkoxide of claim 1 being Nb(butoxyethoxide)$_5$.

14. The metal alkoxyalkoxide of claim 1 being lanthanum (butoxyethoxide)$_3$.

15. The metal alkoxyalkoxide of claim 1 being ruthenium (butoxyethoxide)$_4$.

16. The metal alkoxyalkoxide of claim 1 being cobalt (butoxyethoxide)$_2$.

17. The metal alkoxyalkoxide of claim 1 being lead (butoxyethoxide)$_2$.

* * * * *